(12) United States Patent
McBride-Gagyi et al.

(10) Patent No.: US 11,672,875 B2
(45) Date of Patent: Jun. 13, 2023

(54) NANOPARTICLE-ALGINATE GELS FOR X-RAY IMAGING OF THE VASCULATURE

(71) Applicant: Saint Louis University, St. Louis, MO (US)

(72) Inventors: Sarah McBride-Gagyi, St. Louis, MO (US); Steven W. Buckner, St. Louis, MO (US); Paul Jelliss, St. Louis, MO (US); Mohammad Salauddin Kader, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 17/204,524

(22) Filed: Mar. 17, 2021

(65) Prior Publication Data

US 2022/0296732 A1    Sep. 22, 2022

(51) Int. Cl.
  *A61K 49/04*  (2006.01)
  *B82Y 5/00*  (2011.01)
  *C08L 5/04*  (2006.01)
  *A61K 49/00*  (2006.01)

(52) U.S. Cl.
  CPC ...... *A61K 49/0404* (2013.01); *A61K 49/0428* (2013.01); *A61K 49/0002* (2013.01); *B82Y 5/00* (2013.01); *C08L 5/04* (2013.01)

(58) Field of Classification Search
  CPC ............ A61K 49/0404; A61K 49/0428; A61K 49/0002; B82Y 5/00; C08L 5/04
  See application file for complete search history.

(56) References Cited

U.S. PATENT DOCUMENTS 7,575,734 B2    8/2009  Berkei et al.
9,884,026 B2    2/2018  Fahmy et al.
2011/0104052 A1    5/2011  Barnett et al.
2016/0089454 A1*   3/2016  Andresen ........... A61K 49/0457
                                            424/9.4
2019/0000361 A1*   1/2019  McShane .......... H01L 31/02322
2021/0244374 A1*   8/2021  Zhao ..................... A61B 6/483

FOREIGN PATENT DOCUMENTS

WO    WO-2008084028 A2 *  7/2008  ......... A61K 49/0404

OTHER PUBLICATIONS

Skapin et al., Journal of Colloid and Interface Science, 2010, 324, p. 221-22. (Year: 2010).*
Tryfon et al., ACS Applied Nano Materials, 2019, 2(6), p. 3870-3881. (Year: 2019).*
Constant et al., Preparation, characterization, and evaluation of radiopaque hydrogel filaments for endovascular embolization; J. Biomed. Mater. Res. B. Appl. Biomater.; 2009, vol. 89, No. 2, pp. 306-313 (Abstract only).
Thanoo et al., Radiopaque hydrogel microspheres; J Microencapsul, 1989, vol. 6, No. 2, pp. 233-244 (abstract only).
Tian et al., Radiopaque nano and polymeric materials for atherosclerosis imaging, embolization and other catheterization procedures; Acta Pharmaceutica Sinica B; 2018, vol. 8, No. 3, pp. 360-370 (abstract only).

* cited by examiner

*Primary Examiner* — Michael G. Hartley
*Assistant Examiner* — Leah H Schlientz
(74) *Attorney, Agent, or Firm* — Stinson LLP (57) ABSTRACT

Disclosed are capped nanoparticles that are effectively trapped within an aqueous gelling solution to produce stable gels and function as a contrast agent for vascular imaging. The contrast agent has good radioopacity, is inexpensive to produce, and is safe to handle. This provides a new method to image the fine vasculature of biological systems.

16 Claims, 13 Drawing Sheets

NANOPARTICLE-ALGINATE GELS FOR X-RAY IMAGING OF THE VASCULATURE

CROSS-REFERENCE TO RELATED APPLICATIONS

This application claims priority to U.S. Provisional Patent Application No. 62/990,768, filed on Mar. 17, 2020, which is hereby incorporated by reference in its entirety.

BACKGROUND OF THE DISCLOSURE

The present disclosure relates generally vascular imaging. In particular, the present disclosure is directed to nanoparticle-containing composite gels for improved imaging the vasculature of biological systems using X-ray techniques.

Vascular imaging is a very important technique to distinguish the vascular network with similar or low X-ray attenuation. The contrast agent is critical for this technique. Unstable contrast agent can easily dissociate or leach from the host matrices, which can lead to fuzzy imaging and misdiagnosis. Also, the lack of inherent radiopaque agents has severely hindered the imaging technique.

Barium sulfate is a commonly used contrast agent clinically for gastrointestinal imaging and is much more radiodense than bone. However, commercially available barium sulfate particles are already approaching the size of capillaries and tend to bind in solution to make even larger objects. Thus, the particles clog at the capillary level, never enter the venous system, and the pressure ultimately ruptures the aorta.

Accordingly, there exists a need for new and alternative contrast agents for imaging vasculature, particularly vasculature within and in proximity to bone.

BRIEF DESCRIPTION OF THE DISCLOSURE

In one aspect, the present disclosure is directed to a contrast agent comprising a nanoparticle, the nanoparticle comprising at least one of a barium sulfate ($BaSO_4$) core, a barium carbonate ($BaCO_3$) core, a calcium carbonate ($CaCO_3$) core; and a capping agent comprising at least one of an oligomer and a polymer; and a gel precursor solution.

In one aspect, the present disclosure is directed to a method for imaging vasculature of a subject, the method comprising: introducing into the subject's vasculature a contrast agent, the contrast agent comprising a nanoparticle, the nanoparticle comprising at least one of a barium sulfate ($BaSO_4$) core, a barium carbonate ($BaCO_3$) core, a calcium carbonate ($CaCO_3$) core; and a capping agent comprising at least one of an oligomer and a polymer; and a gel precursor solution, the nanoparticle dispersed in the gel precursor solution; crosslinking the gel precursor solution to produce a gel, wherein the nanoparticle is dispersed in the gel; and imaging the subject using an X-ray technique.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A-1D depict the gelation process.

DETAILED DESCRIPTION

Figure 1A:
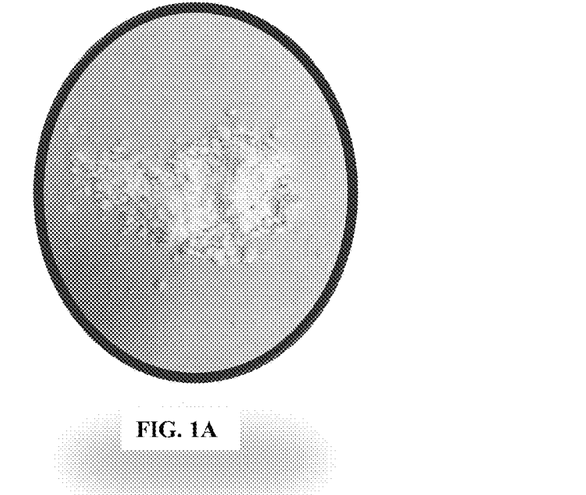
FIG. 1A is a photograph of polyethylene-glycol barium sulfate nanoparticles (PBNPs) powder.
Figure 1B:
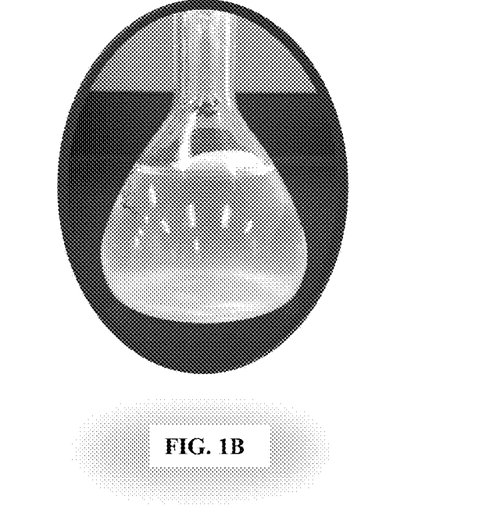
FIG. 1B is a photograph of 2% sodium-alginate (Na-Alginate) solution.
Figure 1C:
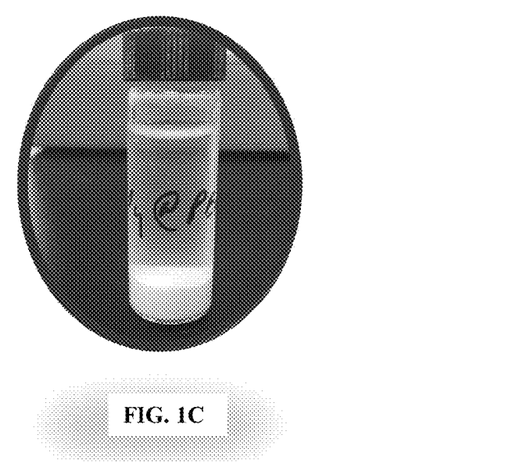
FIG. 1C is a photograph of PBNPs in water.
Figure 1D:
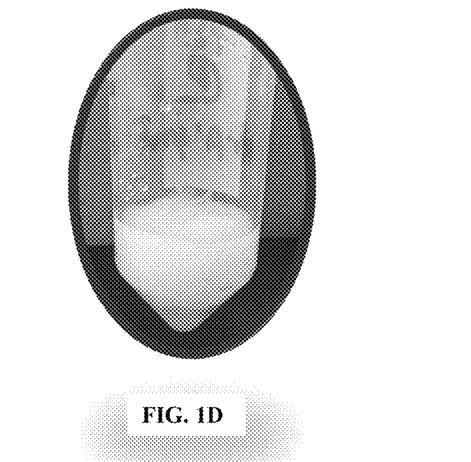
FIG. 1D is a photograph of PBNPs in 2% Na-Alginate solution.
Figure 2:
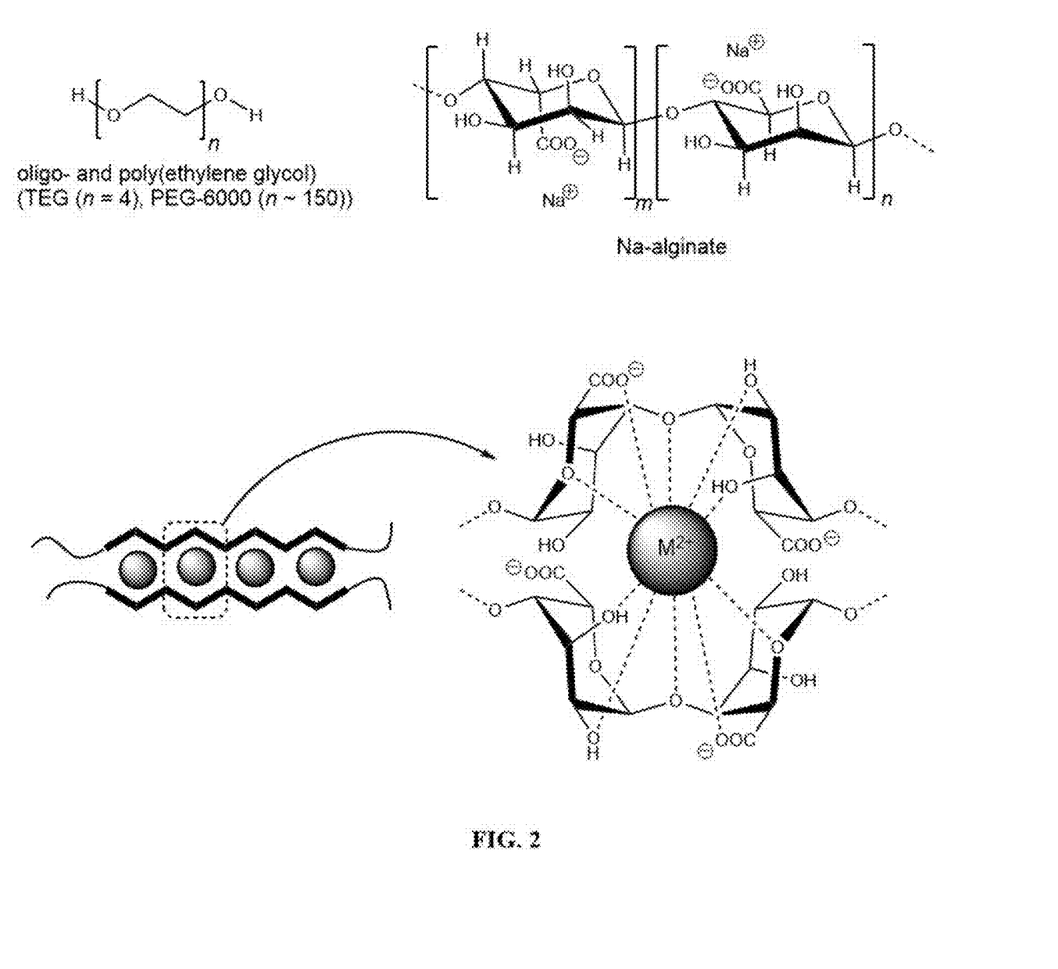
FIG. 2 depicts the proposed mechanism of crosslinking of Na-Alginate with $Ba^{2+}$ or $Ca^{2+}$ cations as explained by the "Egg box model".
Figure 3:
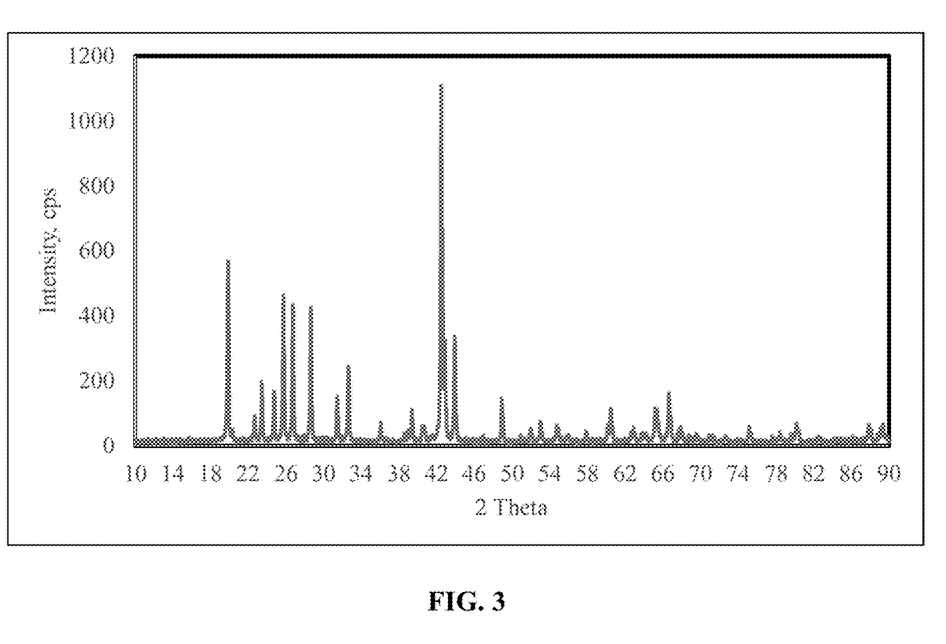
FIG. 3 depicts a PXRD pattern of $BaSO_4$ nanoparticles capped with TEG (crystallite cores=31 nm in diameter).
Figure 4:
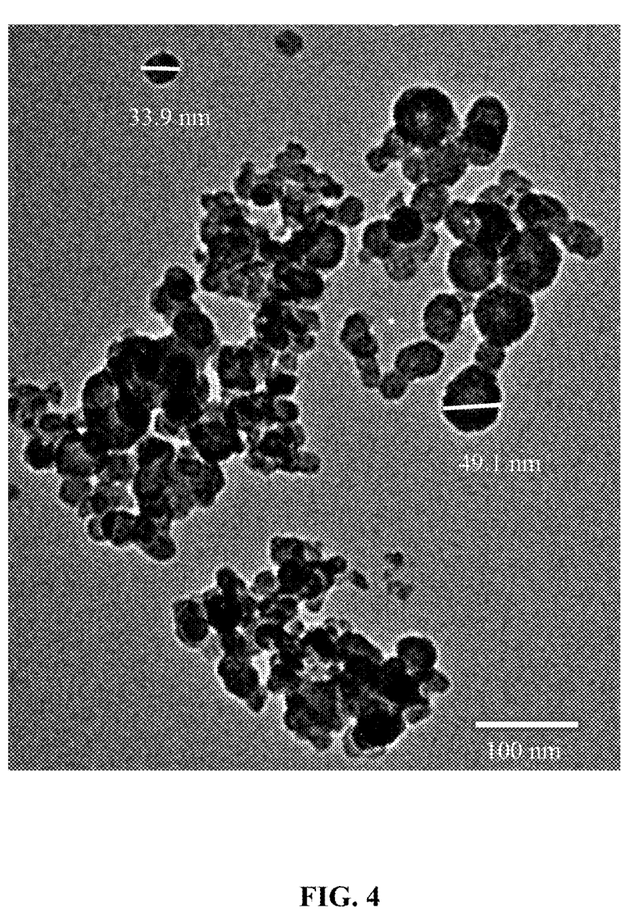
FIG. 4 is a transmission electron micrograph of $BaSO_4$ nanoparticles capped with TEG.
Figure 5:
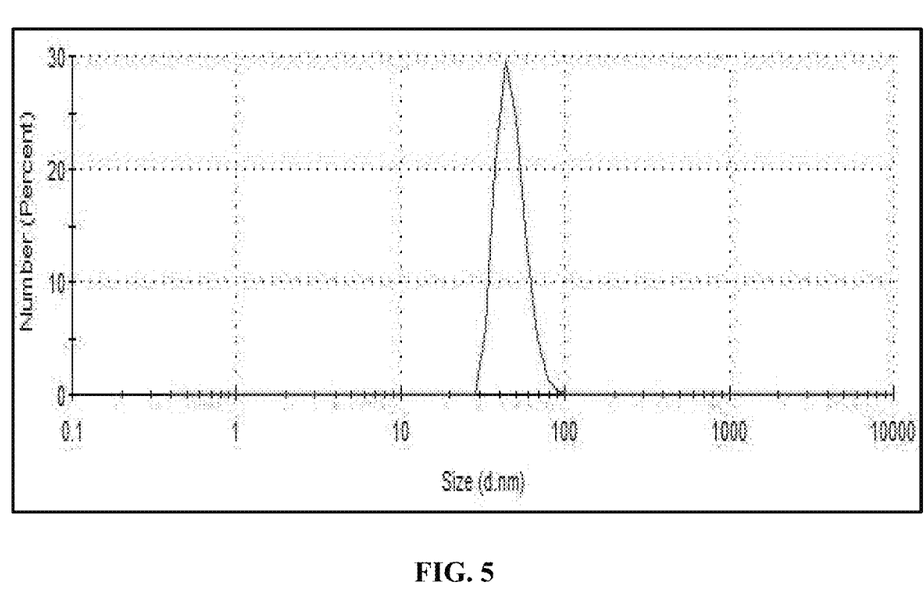
FIG. 5 depicts a DLS measurement of $BaSO_4$ nanoparticles capped with TEG and shows an agglomerated particle size of 50 nm in diameter.
Figure 6:
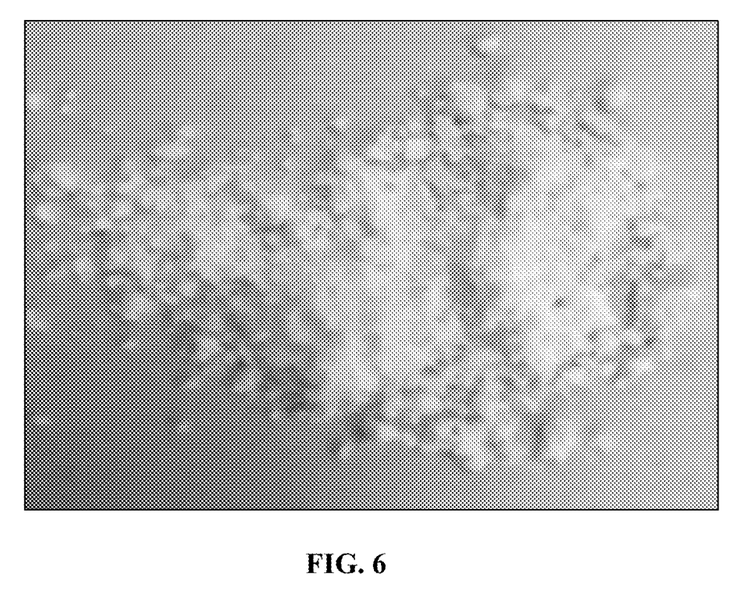
FIG. 6 is a photograph of dry $BaSO_4$@TEG powder.
Figure 7A:
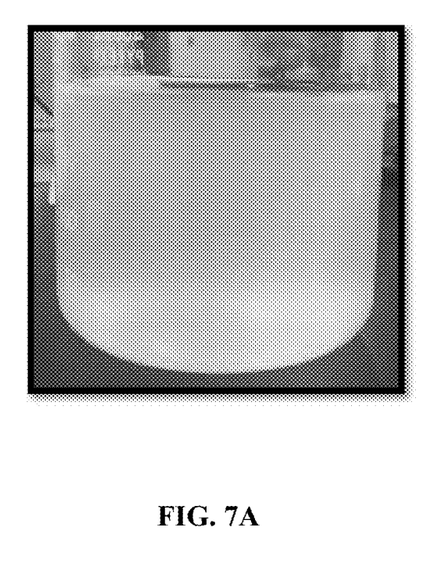
FIGS. 7A & 7B are photographs of a beaker with a solution of $BaSO_4$ nanoparticles in TEG showing well dispersed homogenous $BaSO_4$ nanoparticles in TEG (FIG. 7A) and a concentrated mixture of homogenous $BaSO_4$ nanoparticles in TEG (FIG. 7B).
Figure 7B:
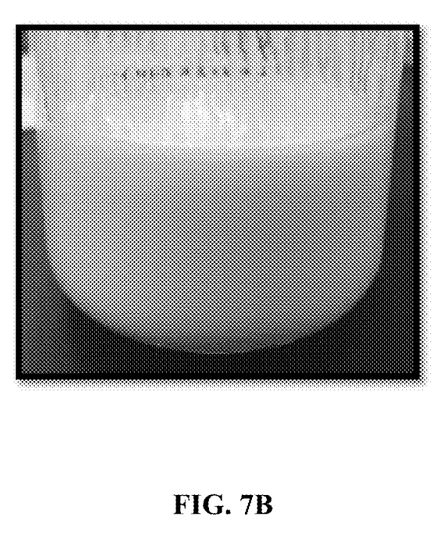
Figure 8:
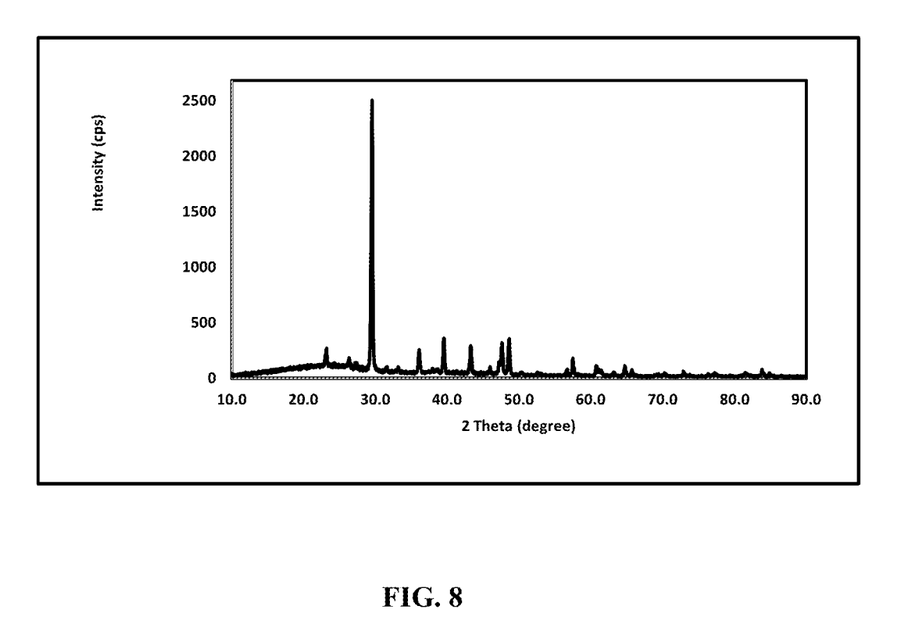
FIG. 8 depicts a PXRD pattern of $CaCO_3$ particles capped with TEG (crystallite cores=41.4 nm in diameter)
Figure 9:
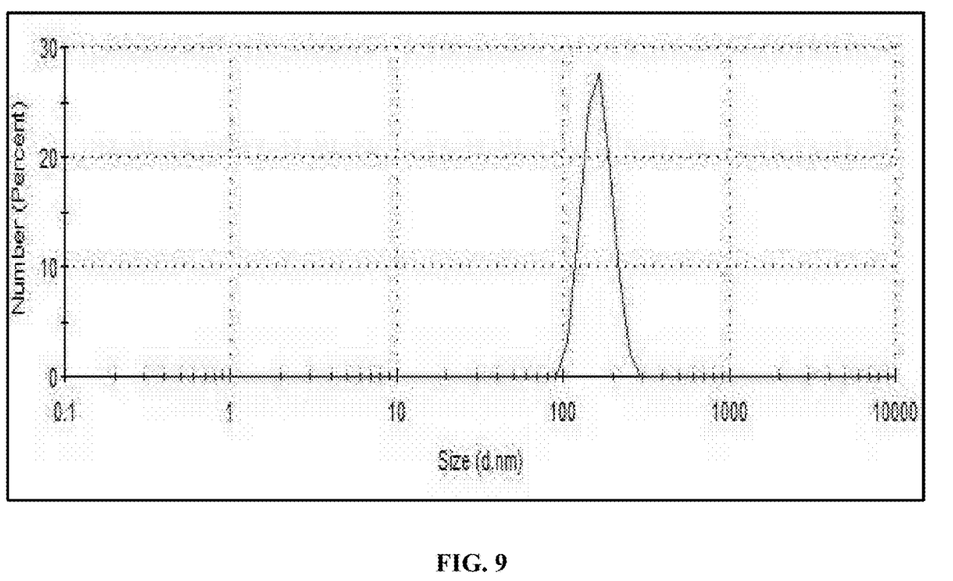
FIG. 9 depicts a DLS measurement of $CaCO_3$ particles capped with TEG and shows an agglomerated particle size of 164 nm in diameter.
Figure 10:
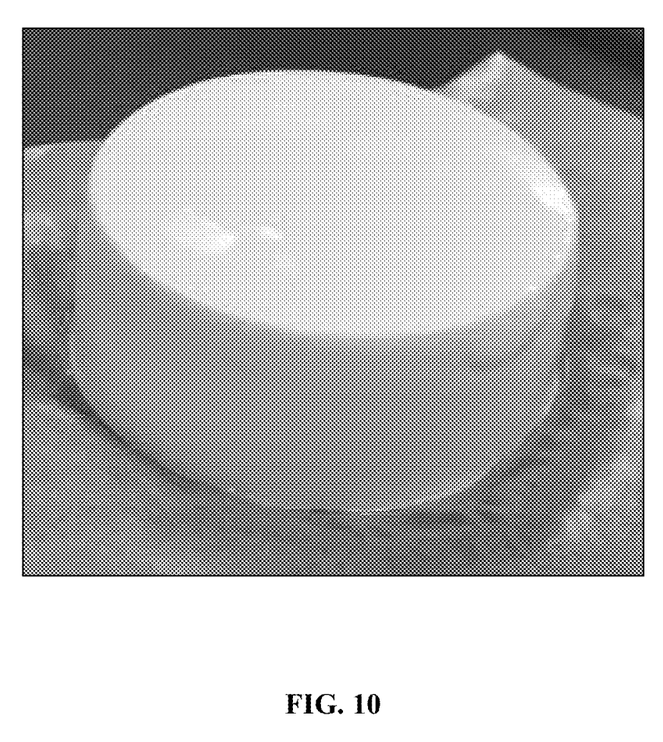
FIG. 10 depicts a $BaSO_4$@TEG, Na-Alginate, Polyacrylic acid sodium salt (PAA), $CaCO_3$ and GDL composite gel.
Figure 11:
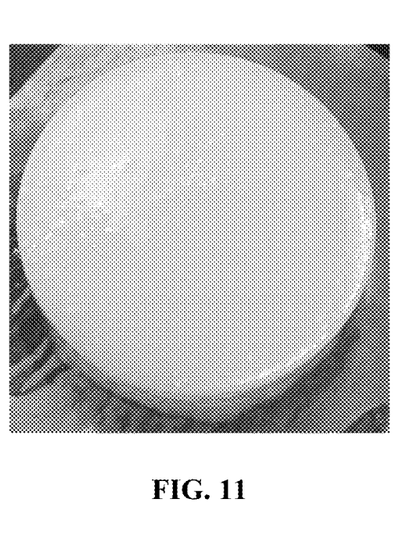
FIG. 11 depicts a $BaSO_4$@TEG, Na-Alginate, Polyvinyl alcohol (PVA) sodium salt (PAA), $CaCO_3$ and GDL composite gel.
Figure 12:
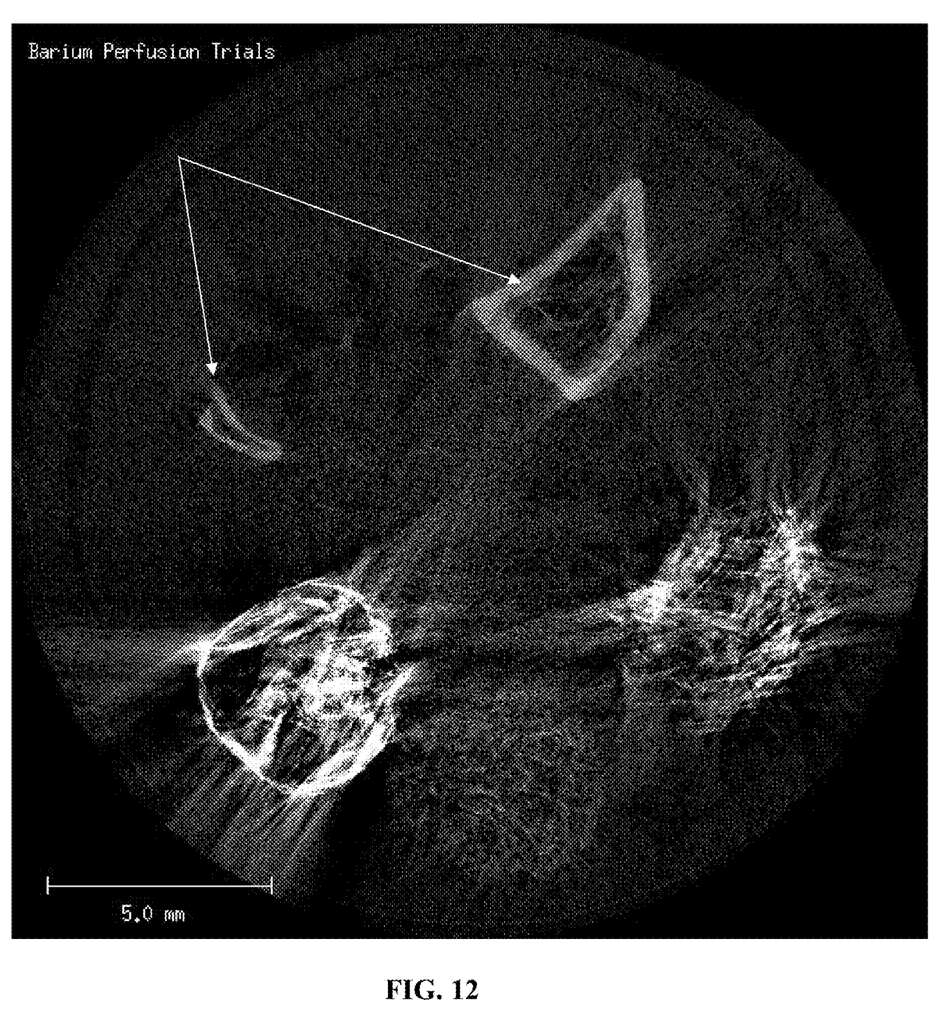
FIG. 12 is an X-ray image of a 1% (wt/wt) gel with 0.05 g/mL, 0.1 g/mL, and 0.25 g/mL of $BaSO_4$ nanoparticles in comparison with bone.
Figure 13:
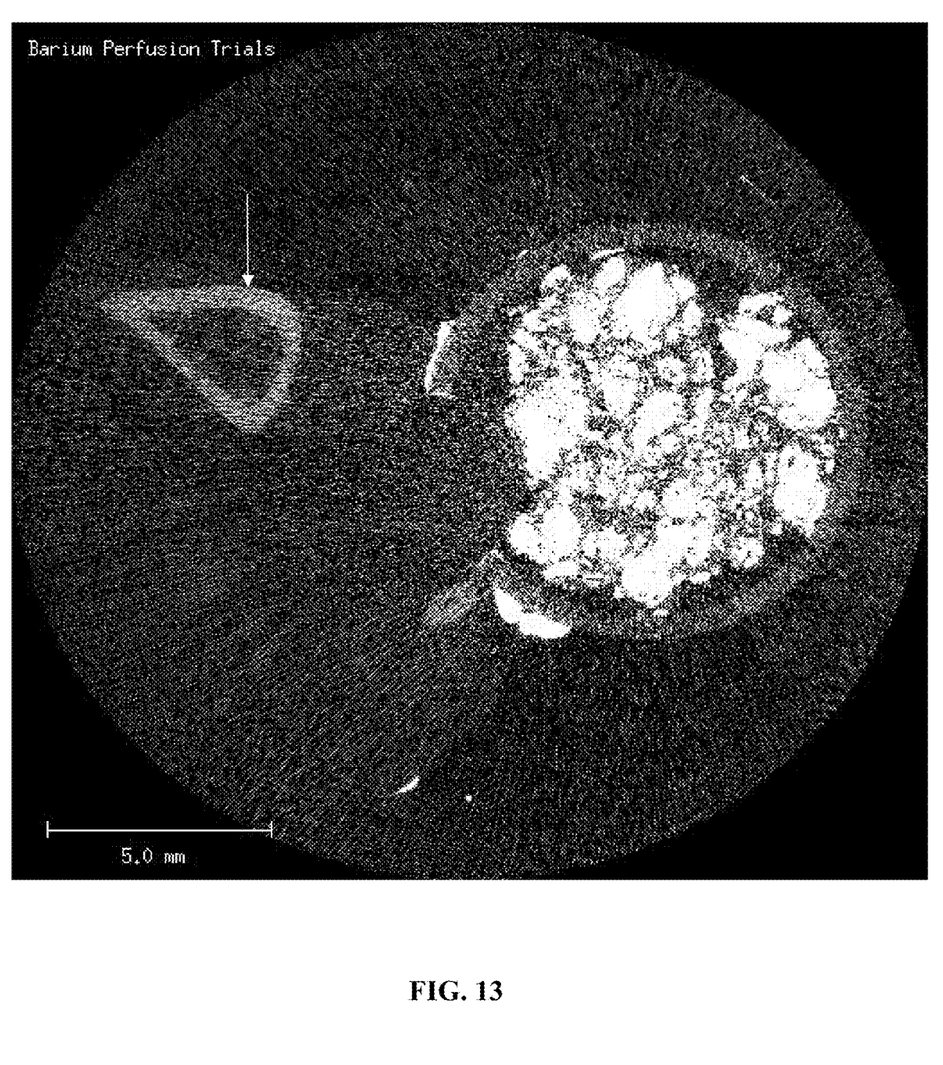
FIG. 13 is an X-ray image of a 2% (wt/wt) gel with 0.5 g/mL of $BaSO_4$ nanoparticles in comparison with bone.

Unless defined otherwise, all technical and scientific terms used herein have the same meaning as commonly understood by one of ordinary skill in the art to which the disclosure belongs.

In one aspect, the present disclosure is directed to an injectable contrast agent. The contrast agent includes a nanoparticle core capped with a capping agent; and a gel precursor solution.

Suitable nanoparticle core materials include a barium sulfate ($BaSO_4$) core, a barium carbonate ($BaCO_3$) core, and a calcium carbonate ($CaCO_3$) core, and combinations thereof.

Suitable capping agents for capping the core material include oligomers, polymers, and combinations thereof. Suitable polymers include polyethylene glycol (PEG) including PEG-600 to PEG-500,000. Other suitable polymers include: polyvinyl alcohol (PVA), polyacrylic acid (PAA), polyacrylamide (PAM), poly(sodium 4-styrenesulfonate) (PSS), for example. Chain-end modified PEG can also be used such as, for example, those with amino $NH_2$ groups and hydroxyl OH groups. Low molecular weight oligoethers (oligomers related to PEG) include triethethylene glycol and tetraethylene glycol are also suitable capping agents.

The nanoparticle core is capped with a capping agent including oligomers, polymers, and combinations thereof as described herein. As used herein, "capping" and "capped" by the oligomer and polymer capping agents provides a homogenous but semi-permeable layer, tightly bound around the ionic nanoparticle core. The underlying ionic structure is thermodynamically stable, but capping imparts favorable characteristics to the nanoparticle core such as permitting dispersion in aqueous media. Without being bound by theory, the capping oligomer and polymer binds to the nanoparticle core surface via predominantly ion-dipole interactions.

The gel precursor solution includes a material that forms a gel (a "gel forming material") upon crosslinking. So the contrast agent is injectable, the gel precursor solution provides a matrix that carries the oligomer- and polymer-capped core nanoparticles to a local tissue site in the subject. Upon gelation, the gel precursor solution forms a gel and retains the nanoparticles in the local tissue site. Suitable gel forming materials include alginate. Other suitable gelling agents include that do not require heating above 50° C., for example, chitosan, silicon-based sol-gels, and gellan gum. Suitably, the amount of alginate in the final alginate composition of the resulting contrast agent can range from about 0.05% (wt/wt) to about 5% (wt/wt). Preferably, the amount of alginate can range from about 0.1% (wt/wt) to about 2% (wt/wt).

In addition to contrast agents where all of the core particles are prepared using the same core material and have the same capping agent, different combinations of materials are also contemplated herein. Different combinations of materials include combinations of different core materials (e.g., $BaCO_3$ cores, $BaSO_4$ cores, $CaCO_3$ cores) with the same or different capping oligomers and capping polymers (e.g., PEG, TEG). For example, $BaCO_3$ cores capped with PEG can be combined with $BaCO_3$ cores capped with TEG, which are then combined with the gel precursor solution to prepare the contrast agent. Similarly, $BaCO_3$ cores capped with PEG can be combined with $BaSO_4$ cores capped with PEG, which are then combined with the gel precursor solution to prepare the contrast agent. $BaCO_3$ cores capped with PEG can be combined with $BaCO_3$ cores capped with TEG and combined with $CaCO_3$ cores capped with TEG, which are then combined with the gel precursor solution to prepare the contrast agent. Thus, exemplary contrast agents include $BaSO_4$-PEG, $BaSO_4$-TEG, $BaCO_3$-PEG, $BaCO_3$-TEG, $CaCO_3$-PEG, $CaCO_3$-TEG, $BaSO_4$-PEG/TEG+/–$BaCO_3$-PEG/TEG+/–$CaCO_3$-PEG/TEG, and $BaCO_3$-PEG/TEG+/–$CaCO_3$-PEG/TEG.

Suitably, the amount of nanoparticle core in the contrast agent can range from about 0.05 g/mL to about 1 g/mL. Suitably, the diameter of the core particles ranges from about 10 nm to about 500 nm. Particle size can be determined by methods known to one skilled in the art such as by Dynamic light scattering (DLS), powder X-ray diffraction (PXRD), transmission electron microscopy, and combinations thereof, for example.

The nanoparticle cores are capped with a capping agent resulting in the formation of the core-shell nanoparticles. As discussed herein, capping of the core particles with a capping agent stabilizes the core and also confers water dispersibility to the system. The amount of capping agent used in the solution for capping ranges from about 0.05% (w/w) to about 30% (w/w). A particularly suitable range of PEG is a range of about 2% (w/w) to about 25% (w/w). A particularly suitable range of TEG is a range of about 0.05% (w/w) to about 30% (w/w), including a range of about 0.05% (w/w) to about 10% (w/w). A particularly suitable amount of PEG is about 2% (w/w). An aqueous capping agent solution is used to synthesize the nanoparticle composites. The amount of capping agent for the capped cores can be determined by elemental analysis.

The contrast agent can further include at least a second polymer to improve gel stiffness. Suitable second polymers include polyacrylic acid (PAA), polyvinyl alcohol, chitosan, and combinations thereof.

The contrast agent can further include a chelating gelation control reagent for controlling gel formation of the contrast agent. Suitable chelating gelation control reagents include ethylenediaminetetraacetic acid (EDTA) and/or glucono-δ-lactone (GDL) in combination with a calcium carbonate. Other suitable chelating gelation control reagents include: nitrilotriacetic acid (NTA), trans-1,2-diaminocylco-hexanetetraacetic acid (DCTA), diethlyenetriaminepentaacetic acid (DTPA), and bis(aminoethyl)glycolether-N,N,N',N'-tetraacetic acid (EGTA).

The polymer- or oligomer-capped core nanoparticles are effectively trapped within a rigid gel that forms from an aqueous solution by crosslinking $Ca^{2+}$ ions with gelling polymers such as alginate. Alternatively, $Cu^{2+}$, $Zn^{2+}$, or $Mg^{2+}$ ions may be used as a crosslinker in place of $Ca^{2+}$.

In one aspect, the present disclosure is directed to a method for imaging vasculature of a subject. The method includes: introducing into the subject's vasculature a contrast agent, the contrast agent comprising a nanoparticle, the nanoparticle comprising a core capped with a capping agents; and a gel precursor solution, the nanoparticle dispersed in the gel precursor solution; crosslinking the gel precursor solution to produce a gel, wherein the nanoparticle is dispersed in the gel; and imaging the subject using an X-ray technique.

Suitable materials for the nanoparticle core are described herein.

Suitable capping agents for capping the core are described herein.

Suitable gel forming materials are described herein.

Suitable subjects include animals. Particularly suitable subjects are cadavers, primates, mice, rats, rabbits, birds, and other animals, particularly laboratory research animals. Suitable subjects can be animals suffering from a disease or disorder that would require the use of the contrast agent to image a tissue site. Introducing the contrast agent into the subject's vasculature is through perfusion, particularly post-mortem perfusion.

The gelation rate of the contrast agent can be controlled. Gelation rate is controlled to allow sufficient time for the contrast agent to be introduced into the vasculature of the subject before crosslinking into a gel. Thus, the method can further include adding a chelating gelation control reagent for controlling gelation time to one of the crosslinker and the gel precursor solution. Gelation rates can range from about 10 seconds to about 48 hours at a temperature ranging from about 5° C. to about 40° C. and within a pH ranging from about 5.0 to about 7, including from about 5.5 to about 6.5. Gelation time can be controlled by adding a 0.1 M solution of EDTA to the gel precursor solution, for example. A suitable alternative to EDTA is calcium carbonate in combination with glucono-δ-lactone. The ratio of $Ca^{2+}$ ions to GDL can be used to control gelation time. In an exemplary gel composition the amounts include 0.5% w/w $CaCO_3$ and 1.5% w/w GDL (the mass % for the whole gel including $CaCO_3$, GDL, Na-alginate, PEG-capped $BaSO_4$ nanoparticles, and also water). A suitable range is from about 0.1% w/w to about 1.0% w/w $CaCO_3$ and also from about 0.3% w/w to about 3.0% w/w GDL (see Table 1). Table 1 also provides an exemplary embodiment using $CaCO_3$/GDL.

TABLE 1

| Contrast Agent | | |
|---|---|---|
| Gel Component | % (w/w) | % (w/w) Range |
| CaCO₃ | 0.5 | 0.1-1.0 |
| GDL | 1.5 | 0.3-3.0 |
| Na-alginate | 1.0 | 0.05-5.0 |
| PEG-BNPs | 9.5 | 5.0-15.0 |
| Water | 88.0 | 75.0-95.0 |

Other suitable chelating gelation control reagents include: nitrilotriacetic acid (NTA), trans-1,2-diaminocylcohexanetetraacetic acid (DCTA), diethlyenetriaminepentaacetic acid (DTPA), and bis(aminoethyl)glycolether-N,N,N',N'-tetraacetic acid (EGTA).

The radioopacity of the contrast agent can be controlled by adjusting the concentration of capped nanoparticles in the gel solution. Suitably, the concentration of capped nanoparticles ranges from about 0.05 g/mL to about 1 g/mL.

EXAMPLES

Example 1

Materials and Methods

The nanoparticle core structure was produced using an arrested precipitation reaction. The foundational precipitation process is as follows:

The BaSO₄(s) core particles are capped with the PEG polymer units that serve to control the precipitation reaction. This process produces the PEG-capped BaSO₄ structure that is used to form and provide contrast in the final gel structure.

The step-by-step synthesis for each component in the final X-ray contrast agent is given next. Amounts listed are for a typical synthesis and are not limiting on the disclosure. These amounts are only provided as typical examples.

Synthesis of PEG-BaSO₄ NPs (PBN)

Materials:
0.01 M Na₂SO₄ solution
0.01 M Ba(NO₃)₂ solution
Polyethylene glycol (PEG-6000)

Procedure

Barium Sulfate synthesis can be carried out by the precipitation reaction:

$$Ba(NO_3)_2(aq) + Na_2SO_4(aq) = BaSO_4(ppt) + 2NaNO_3(aq)$$

To prevent bulk barium sulfate formation, capping agent (PEG-6000) was added during the precipitation process. First, 0.01 M Na₂SO₄ solution was prepared in a 100 mL volumetric flask using DI water. Na₂SO₄ was required approximately 0.1420 gm. Then, 0.01 M Ba(NO₃)₂ solution was prepared in another 100 mL volumetric flask using DI water. Ba(NO₃)₂ was required approximately 0.2613 gm. 100 mL of 0.01 M Na₂SO₄ was taken in a 500 mL beaker and approximately 2 mg of the PEG-6000 was added to the solution with continuous stirring to completely dissolve the PEG in the 0.01 M Na₂SO₄ solution. Then, previously prepared 0.01 M Ba(NO₃)₂ solution was added to the PEG-0.01 M Na₂SO₄ solution dropwise with continuous stirring at a room temperature to get the PEG-BaSO₄ NPs. PEG-BaSO₄ NPs solution was dried in the oven at (80-100)° C. for about 10-12 hours to obtain a PEG-BaSO₄ nanoparticle powder.

Preparation of the Gel

Materials required for the gelling process:
1% Na-Alginate
PBN powder
0.01 M EDTA Procedure

First, 1 gm of Na-Alginate was added to the 100 mL DI water to prepare 1% Na-Alginate. Then, 0.01 M EDTA was prepared in a 100 mL volumetric flask from 0.1022 M stock solution. Approximately 0.1 gm of the PEG-BaSO₄ NPs powder was dissolved in the 0.5 mL 0.01 M EDTA solution in a small vial. Micropipette was used to transfer the solution. The solution was then sonicated for about 5 minutes to dissolve the NPs powder in the 0.01 M EDTA solution. Finally, 0.5 mL of the 1% Na-Alginate solution was added to the PEG-BaSO₄-EDTA solution to make the gel. Gelling time was recorded using stopwatch. EDTA concentration can be varied to control the gelling time.

Example 2

Synthesis of TEG@BaSO₄NPs:

Materials and Methods
2.61 M Na₂SO₄
0.61 M Ba(NO₃)₂
44% Tetra ethylene Glycol (TEG)

Barium Sulfate synthesis was be carried out by the precipitation reaction:

$$Ba(NO_3)_2(aq) + Na_2SO_4(aq) \rightarrow BaSO_4(s) + 2NaNO_3(aq)$$

10 g of Na₂SO₄ was dissolved in 27 mL of DI water to make 2.61 M Na₂SO₄. 16 g of Ba(NO₃)₂ was dissolved in 100 mL of DI water to make 0.61 M Ba(NO₃)₂. Both beakers were placed on hot plates set to high and mixed using a glass rod. Once the Na₂SO₄ was completely dissolved, it was moved to another hot plate on a lower heat setting. In order to prevent bulk barium sulfate formation, capping agent TEG was added during the precipitation process. 100 mL of TEG was mixed with the dissolved 100 mL of Ba(NO₃)₂ with a glass rod. A sonic dismembrator was used on the TEG and Ba(NO₃)₂ solution while adding the Na₂SO₄ dropwise with a Pasteur pipette. The sonic dismembrator was tuned so that it was highly pitched and visibly mixing the solution (this was readjusted throughout the addition). Drops were added closest to the sonic dismembrator probe at a rate of 2 drops per second. After each full dispense of the pipette, the beaker was moved so that the probe reached the edges in a circular twisting motion and was then returned to the middle of the beaker. If the Na₂SO₄ happened to crash out of solution, it was placed on the hot plate again and redissolved. Once all of the solutions were combined under the sonic dismembrator, a watch glass was placed on top of the beaker holding the BNP's suspended in TEG. TEG@BaSO₄NPs solution was dried in an oven at (80-100)° C. for about 10-12 hour to obtain the TEG@BaSO₄NPs powder.

TABLE 2

TEG@BaSO$_4$ NPs

| Ba(NO$_3$)$_2$ | NaSO$_4$ | Tetra ethylene Glycol (TEG) | Water |
|---|---|---|---|
| 0.61M | 2.61M | 44% | 300 mL |

TABLE 3

Composition of TEG@BaSO$_4$ NPs and possible composition ranges

| Material | Mass w/w % Composition[a] | Possible w/w % Range[b] |
|---|---|---|
| TEG | 0.36 | 0.05-10 |
| BaSO$_4$ | 99.64 | 90-99.95 |

[a]The above described synthesis produced a TEG@BaSO$_4$ NPs with this mass % composition (as estimated from DSC-TGA).
[b]Synthetic quantities can be adjusted to produce TEG@BaSO$_4$ NPs with composition that falls within each range.

Example 3

Synthesis of TEG@CaCO$_3$ NPs:
  Materials required for the synthesis process:
  4.50 M CaCl$_2$
  2.36 M Na$_2$CO$_3$
  94% Tetra ethylene Glycol (TEG)
  Calcium Carbonate Nanoparticles:

$$CaCl_2(aq)+Na_2CO_3(aq) \rightarrow CaCO_3(s)+2NaCl(aq)$$

0.5 g of CaCl$_2$ was weighed into a glass vial and dissolved in 1 mL of DI water by shaking to obtain a 4.5 M CaCl$_2$ solution. 0.5 g of Na$_2$CO$_3$ was weighed into a glass vial and dissolved in 2 mL of DI water by shaking to obtain a 2.36 M Na$_2$CO$_3$ solution. 50 mL of TEG was mixed with the dissolved 1 mL CaCl$_2$ solution with a glass rod. A sonic dismembrator was used on the TEG and CaCl$_2$ solution while adding the Na$_2$CO$_3$ dropwise with a Pasteur pipette. The sonic dismembrator was tuned so that it was highly pitched and visibly mixing the solution. Drops were added closest to the sonic dismembrator probe at a rate of 2 drops per second. After addition was completed, the beaker was moved so that the probe reached the edges in a circular twisting motion and was then returned to the middle of the beaker. Once all of the solutions were combined under the sonic dismembrator, a watch glass was placed on top of the beaker holding the calcium carbonate nanoparticles suspended in TEG.

TABLE 4

TEG@CaCO$_3$ NPs

| CaCl$_2$ | Na$_2$CO$_3$ | Tetra ethylene Glycol (TEG) | Water |
|---|---|---|---|
| 4.50M | 2.36M | 94% | 50 mL |

TABLE 5

Compositions of TEG@ CaCO$_3$ NPs and possible composition ranges

| Material | Mass w/w % Composition[a] | Possible w/w % Range[b] |
|---|---|---|
| TEG | 23 | 5-30 |
| CaCO$_3$ | 67 | 70-95 |

[a]The above described synthesis produced a TEG@ CaCO$_3$ NPs with this mass % composition (as estimated from DSC-TGA).
[b]Synthetic quantities can be adjusted to produce TEG@ CaCO$_3$ NPs with composition that falls within each range.

Example 4

Synthesis of 50 mL Nanocomposite Gel:
  Materials required for the synthesis process:
  0.80% Na-Alginate (0.40 gm in 50 mL)
  2.50 gmTEG@BaSO$_4$NPs powder
  0.50 gm Polyacrylic acid (PAA)
  0.50 gm GDL (Glucono-δ-lactone)
  0.20 gm TEG@CaCO$_3$
  1.0 gm Na$_2$SO$_4$ 0.80 gm of Na-Alginate was added to 100 mL DI water to prepare an 0.80% Na-Alginate solution. Approximately 2.50 gm of the TEG@BaSO$_4$ NPs powder was dispersed in 20 mL DI water. Then 0.20 gm of CaCO$_3$ was mixed with the solution. Then 0.50 gm of Polyacrylic acid (PAA) added with the solution. Then 1.0 gm of Na$_2$SO$_4$ was added to the solution. The solution was then sonicated for about 5 minutes to disperse the NPs powder in the solution. Then 25 mL of the 0.80% Na-Alginate solution was added to the TEG@BaSO$_4$ solution. 0.50 gm of GDL (Glucono-δ-lactone) was dissolved in 5.0 mL DI water. Finally, 5.0 mL of the GDL solution was mixed with the 45.0 mL nanocomposite to initiate the crosslinking. Strong acid or strong base may be added to adjust the pH to within the range 5.5-6.5 to optimize crosslinking for most effective gelation. Gelling time was recorded using a stopwatch. GDL, PAA, Na-alginate and CaCO$_3$ concentration was varied to control the gelling time.

TABLE 6 nanocomposite gel (50 mL)

| CaCO$_3$ | BaSO$_4$ | Alginic Acid, Sodium Salt | Glucono-δ-lactone (GDL) | Poly (acrylic acid sodium salt) (PAA) | Na$_2$SO$_4$ | Gelation time |
|---|---|---|---|---|---|---|
| 0.20 gm | 2.5 gm | 0.40 gm | 0.50 gm | 0.50 gm | 1.0 gm | 30-35 min. |

TABLE 7

Composition and composition ranges for the gel

| Material | Mass w/w % Composition[a] | w/w % Range[b] | Notes |
|---|---|---|---|
| Na-Alginate | 0.025 | 0.01-0.1 | |
| TEG@BaSO$_4$ NPs | 4.5 | 1-50 | |
| Polyacrylic acid | 0.91 | 0.5-5 | c |
| Glucono-d-lactone | 0.91 | 0.01-5 | d |
| TEG@CaCO$_3$ NPs | 0.36 | 0.01-5 | d |
| Na$_2$SO$_4$ | 1.8 | 0-10 | |

[a] The above described synthesis produced a gel with this mass % composition (water not listed but makes up the remaining % mass).
[b] Synthetic quantities can be adjusted to produce a gel with composition that falls within each range. Water makes up any remaining mass.a
c Polyvinyl alcohol can replace Polyacrylic acid - both should be included in coverage.
d The gelling time for the gel synthesized above (with 0.36 w/w % CaCO$_3$ and 0.91 w/w % GDL) is 30 minutes. Adjustment of these compositional quantities can vary the gelling time from <1 minute to 24 hours.

The present disclosure provides a contrast agent embedded in an injectable polymeric matrix that can be delivered with a small-gauge needle that is minimally invasive. A novel nanoparticle structure is provided that effectively reacts with aqueous alginate solutions to produce stable gels and function as a contrast agent that is particularly suitable for vascular imaging. The contrast agent has good radiopacity, is inexpensive to produce, and is safe to handle. The material can be introduced into the vasculature of animal systems and provides good X-ray contrast. This provides a new method to image the fine vasculature of biological systems.

What is claimed is:

1. An injectable contrast agent comprising:
a nanoparticle, the nanoparticle comprising
a core comprising at least one of a barium sulfate (BaSO$_4$) core, a barium carbonate (BaCO$_3$) core, a calcium carbonate (CaCO$_3$) core and combinations thereof; and
a tetra (ethylene glycol) capping agent; and
a gel precursor solution.

2. The contrast agent of claim 1, wherein the gel precursor solution is an alginate gel precursor solution.

3. The contrast agent of claim 1, wherein the amount of nanoparticle ranges from about 0.05 g/mL to about 1 g/mL.

4. The contrast agent of claim 1, wherein the core diameter ranges from about 50 nm to about 500 nm.

5. The contrast agent of claim 1, wherein the tetra (ethylene glycol) capping agent ranges from about 0.05% (w/w) to about 30% (w/w).

6. The contrast agent of claim 1, further comprising polyacrylic acid; polyvinyl alcohol, chitosan, and combinations thereof.

7. The contrast agent of claim 1, further comprising a chelating gelation control reagent selected from the group consisting of ethylenediaminetetraacetic acid, glucono-δ-lactone in combination with calcium carbonate, nitrilotriacetic acid, trans-1,2-diaminocylcohexanetetraacetic acid, diethlyenetriaminepentaacetic acid, and bis(aminoethyl)glycolether-N,N,N',N'-tetraacetic acid, and combinations thereof.

8. A method for imaging vasculature of a subject, the method comprising:
introducing into the subject's vasculature an injectable contrast agent, the injectable contrast agent comprising
a nanoparticle, the nanoparticle comprising
a core comprising at least one of a barium sulfate (BaSO$_4$) core, a barium carbonate (BaCO$_3$) core, a calcium carbonate (CaCO$_3$) core and combinations thereof; and
a tetra (ethylene glycol) capping agent; and
a gel precursor solution, wherein the nanoparticle is dispersed in the gel precursor solution; and
imaging the subject using an X-ray technique.

9. The method of claim 8, wherein the gel precursor solution is an alginate gel precursor solution.

10. The method of claim 8, wherein the amount of nanoparticle ranges from about 0.05 g/mL to about 1 g/mL.

11. The method of claim 8, wherein the core diameter ranges from about 50 nm to about 500 nm.

12. The method of claim 8, wherein the tetra (ethylene glycol) capping agent ranges from about 0.05% (w/w) to about 30% (w/w).

13. The method of claim 9, wherein an amount of alginate in the alginate gel precursor solution ranges from about 0.5% (w/w) to about 5% (w/w).

14. The method of claim 8, wherein gelation rate of the gel precursor solution ranges from about 10 seconds to about 48 hours at a temperature ranging from about 5° C. to about 40° C.

15. The method of claim 8, wherein the injectable contrast agent further comprises polyacrylic acid; polyvinyl alcohol, chitosan, and combinations thereof.

16. The method of claim 8, wherein the injectable contrast agent further comprises a chelating gelation control reagent selected from the group consisting of ethylenediaminetetraacetic acid, glucono-δ-lactone in combination with calcium carbonate, nitrilotriacetic acid, trans-1,2-diaminocylcohexanetetraacetic acid, diethlyenetriaminepentaacetic acid, and bis(aminoethyl)glycolether-N,N,N',N'-tetraacetic acid, and combinations thereof.

* * * * *